United States Patent [19]

Haskell et al.

[11] 4,267,180

[45] May 12, 1981

[54] NOVEL ANTIBACTERIAL AMIDE COMPOUNDS AND PROCESS MEANS FOR PRODUCING THE SAME

[75] Inventors: Theodore H. Haskell, Ann Arbor; Marland P. Hutt, Jr., Saline; Ernest D. Nicolaides, Ann Arbor, all of Mich.

[73] Assignee: Warner-Lambert Company, Morris Plains, N.J.

[21] Appl. No.: 117,318

[22] Filed: Jan. 31, 1980

Related U.S. Application Data

[63] Continuation-in-part of Ser. No. 19,984, Mar. 12, 1979, abandoned.

[51] Int. Cl.³ .............. A61K 31/505; C07D 499/68
[52] U.S. Cl. ............... 424/251; 260/239.1; 544/321
[58] Field of Search ............. 260/239.1; 424/251

[56] References Cited

U.S. PATENT DOCUMENTS

| | | | |
|---|---|---|---|
| 3,660,403 | 5/1972 | Shen et al. | 424/251 |
| 3,951,982 | 4/1976 | Goel | 260/239.1 X |
| 3,954,734 | 5/1976 | Doub et al. | 260/239.1 |
| 4,008,220 | 2/1977 | Tobiki et al. | 260/239.1 |
| 4,041,161 | 8/1977 | Kocisis et al. | 424/246 |
| 4,081,441 | 3/1978 | Baker et al. | 260/239.1 |
| 4,156,724 | 5/1979 | Yamada et al. | 424/246 |

*Primary Examiner*—Natalie Trousof
*Assistant Examiner*—Vera C. Clarke
*Attorney, Agent, or Firm*—Stephen Raines

[57] ABSTRACT

Novel organic amide compounds which are N-[2-[(acylaminoacylamino or aminoacylamino)phenyl]-4-hydroxy-5-pyrimidinylcarbonyl] penicillin compounds having broad spectrum antibacterial utility are provided by (a) reacting the free amino acid of the appropriate penicillin or the acid salt or silylated derivative or complex thereof with a reactive derivative of the corresponding N-2-[(acylaminoacylamino or aminoacylamino)phenyl]-4-hydroxy-5-pyrimidine carboxylic acid or (b) reacting the free amino acid of 6-aminopenicillamic acid or a related compound or the acid salt or silylated derivative thereof with a reactive derivative of the corresponding D-N-[2-[(acylaminoacylamino or aminoacylamino)phenyl]-4-hydroxy-5-pyrimidinylcarbonyl]-2-substituted glycine. Pharmaceutical compositions containing said compounds and methods for treating infections using said compositions are also disclosed.

24 Claims, No Drawings

NOVEL ANTIBACTERIAL AMIDE COMPOUNDS AND PROCESS MEANS FOR PRODUCING THE SAME

This is a continuation-in-part of copending United States Application, Ser. No. 19,984, filed Mar. 12, 1979, now abandoned.

SUMMARY AND DETAILED DESCRIPTION

The present invention relates to novel chemical compounds that are useful as pharmacological agents and to methods for their production. More particularly, the invention relates to novel organic amide compounds having the formula

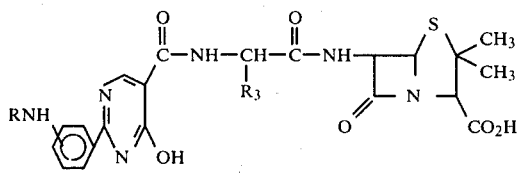

and pharmaceutically acceptable salts thereof, wherein R is

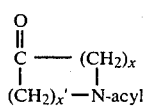

or $R_1[NR_4\text{-acyl}]_n$; x is an integer from one to five, x' is zero, one or two; $R_1$ is hydrogen, lower alkyl, benzyl

wherein $R_2$ is hydrogen, amino or a lower alkyl group of from one to four carbon atoms, optionally substituted by from one to three chlorine or fluorine atoms; $R_4$ is hydrogen or lower alkyl; N-acyl is an aminoacyl moiety derived from a carboxylic acid of from two to ten carbon atoms optionally substituted by from one to three of the following groups, hydroxyl, carboxyl,

formamido, lower alkylamido,

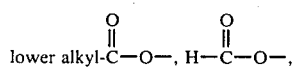

carbamido, lower alkoxy, low alkylthio, amino, carbonyl oxygen, or sulfonic acid; $R_3$ is phenyl, 4-hydroxyphenyl, 2-thienyl or cyclohexa-1,4-dien-1-yl and n is an integer of from one to four. When n is two to four, the acyl groups may be the same or different. When the acyl group is substituted by more than one group, the substituents may be the same or different.

Included within the above definition for N-acyl are cyclic structures incorporating the nitrogen atom by removal of two hydrogen atoms, such as the pyroglutamyl group, prolyl group, etc.

The carbon atoms may be part of a configuration which is classified as an aliphatic, olefinic or aromatic grouping or mixture of both, such as a phenethyl group.

The preferred compounds are those wherein R-NH is in the P position and is an optionally active $R_1$- aminoacyl fragment which is in the L form. The most preferred compounds are those wherein N-acyl is N-acetylglycyl, N-acetyl-L-alanyl, N-propinyl-L-alanyl, N-acetyl-L-glutaminyl, alpha-acetamidoisobutyryl or 5-oxo-L-prolyl: $R_2$ is a carbon fragment of from one to four carbon atoms and $R_3$ is phenyl or 4-hydroxyphenyl and pharmaceutically-acceptable salts thereof.

The term "lower alkyl", where not specifically defined, is defined as a hydrocarbon moiety having from one to six carbon atoms. Lower alkoxy is equivalent to "lower alkyl-O-".

In accordance with the invention the foregoing amide compounds having the formula

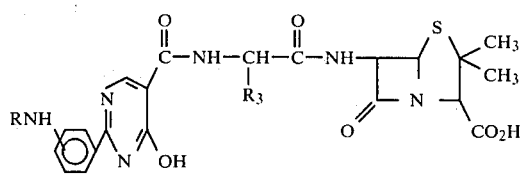

and pharmaceutically acceptable salts thereof wherein R, $R_1$, $R_2$, $R_3$ and $R_4$ are as previously defined are produced by reacting a compound of the formula

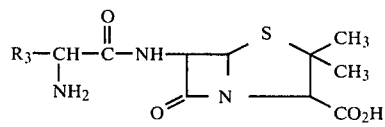

or the basic salt, silylated derivative (preferably the disilylated) or complex (preferably the dimethyl sulfoxide) thereof wherein $R_3$ is as previously defined, with a reactive derivative of a 4-hydroxy-5-pyrimidine carboxylic acid compound having the formula

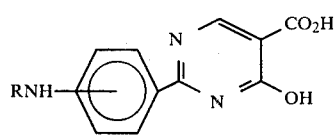

or its acid addition salt, where R, $R_1$, $R_2$ and $R_4$ have the aforementioned significance.

Some examples of reactive derivatives of the 2-substituted-4-hydroxy-5-pyrimidine carboxylic acid compound suitable for the reaction are the acid halides (especially the acid chloride), the imidazolide, mixed anhydrides (especially those formed from an alkyl chloroformate such as methyl, ethyl, and isobutyl chloroformate or pivalyl chloride), and activated esters such as the pentachlorophenyl ester and N-hydroysuccinimide ester.

The reactants are normally employed in approximately equimolar quantities, although an excess of either (4-hydroxy-5-pyrimidine carboxylic acid compound or amino acid compound) can be used if desired. The reaction can be carried out in any of a number of unreactive solvents. When using a silylated derivative for the reaction, the solvent should be anhydrous and may include tertiary amides (such as N,N-dimethylacetamide, dimethylformamide, and N-methyl-2-pyrrolidinone), ethers (such as dioxane, tetrahydrofuran, and 1,2-dimethoxyethane), chlorinated hydrocarbons (such as chloroform and dichloromethane), and mixtures of these. In addition to any of these solvents, when using the penicillin compounds in the free acid or salt form, aqueous solutions may be used for acylation with an acid halide or mixed anhydride under normal Schotten-Baumann conditions. The duration and temperature of the reaction are not critical. Temperatures in the range from −30° to +30° C. are commonly used for reaction times ranging from a few hours up to a day or more. The product may be isolated in any suitable way as the free acid or as a salt by appropriate adjustment of the pH.

The reactive derivative of 2-(substituted)-4-hydroxy-5-pyrimidine carboxylic acid compounds and acid-addition salts which are required as starting materials in the foregoing process can be prepared according to any of a variety of methods.

A 2-(substituted)-4-hydroxy-5-pyrimidine carboxylic acid may be converted to its acid chloride utilizing thionyl chloride, its mixed anhydride utilizing ethyl chloroformate, its pentachlorophenyl ester by esterification with pentachlorophenol and its imidazolide by reacting the acid with 1,1'-carbonyldiimidazole.

Compounds of the formula

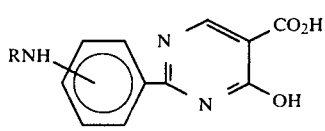

except wherein R is H[NH-acyl], are prepared by acylation of a compound of the formula

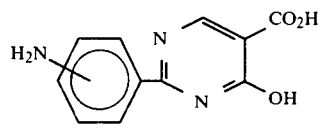

with a compound of the formula

wherein R is as previously defined, except where R is H[NR$_4$-acyl].

The compound of the formula

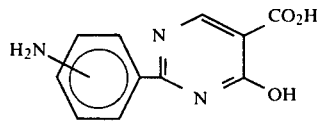

is prepared by hydrolyzing a compound of the formula

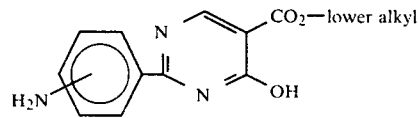

which is in turn prepared by coupling a compound of the formula

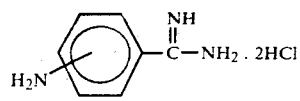

with a compound of the formula lower alkyl-O-CH=C(CO$_2$-lower alkyl)$_2$

The compound of the formula

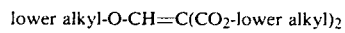

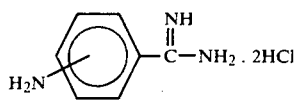

is prepared by reducing a compound of the formula

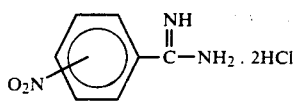

The silylated amino acid starting materials can be prepared by reacting an amino acid of the formula

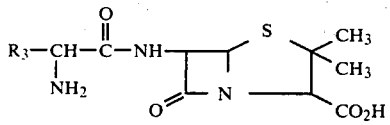

or a salt thereof wherein R$_3$ is as previously defined in anhydrous from with either one or two equivalents of a tri(lower alkyl)silyl chloride in the presence of triethylamine. The preferred silylating agents are trimethylsilyl chloride and dimethyl dichlorosilane. When two equivalents of the silylating agent are used, both the amino and the carboxyl group become silylated. When one equivalent is used, only the carboxyl group is silylated. Both the mono- and disilylated products are fully reactive with the activated acids. The disilylated product is preferred over the monosilylated product as a starting material. After acylation the silyl groups are easily removed by treatment with water.

Also in accordance with the invention, the compounds of this invention may be produced by reacting a free amino acid of the formula

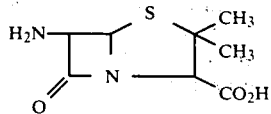

or the corresponding acid salt or silylated derivative thereof with a reactive derivative of D-N-[2-(substituted)-4-hydroxy-5-pyrimidinylcarbonyl]-2-substituted glycine having the formula

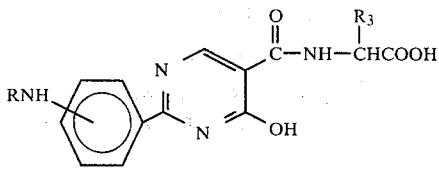

or its acid addition salts where R, $R_1$, $R_2$, $R_3$ and $R_4$ have the aforementioned significance.

Some examples of reactive derivatives of the D-N-[2-(substituted)-4-hydroxy-5-pyrimidinylcarbonyl]-2-substituted glycine compounds suitable for the reaction are the acid halides, mixed anhydrides (especially those formed from an alkyl chloroformate, such as ethyl chloroformate and isobutyl chloroformate), and activated esters, such as the pentachlorophenyl ester and N-hydroxysuccinimide ester. Since racemization is more likely with the acid halide, the other forms are generally preferred. The reactants are normally employed in approximately equimolar quantities, although an excess of either (pyrimidine acid compound or amino acid compound) can be used if desired. The reaction can be carried out in any of a number of unreactive solvents. When using the silylated derivative for the reaction the solvent should be anhydrous and may include tertiary amides (such as N,N-dimethylacetamide, dimethylformamide, and N-methyl-2-pyrrolidinone), ethers (such as dioxane, tetrahydrofuran, and 1,2-dimethoxyethane), chlorinated hydrocarbons (such as chloroform and dichloromethane), and mixtures of these. In addition to any of these solvents, 6-aminopencillanic acid may be reacted with an acid chloride or mixed anhydride in the free acid or salt form using aqueous solutions under normal Schotten-Baumann conditions. The duration and temperature of the reaction are not critical. Temperatures in the range from $-30°$ to $+30°$ C. are commonly used for reaction times ranging from a few hours up to a day or more. The product may be isolated in any suitable way as the free acid or as a salt by appropriate adjustment of the pH.

The reactive derivative of D-N-[2-(substituted)-4-hydroxy-5-pyrimidinylcarbonyl]-2-substituted glycines or their acid-addition salts which are required as starting materials in the foregoing process can be prepared by methods illustrated in greater detail hereinafter.

D-N-[2-(substituted)-4-hydroxy-5-pyrimidinylcarbonyl]-substituted glycine compounds may be prepared by reacting the corresponding reactive derivative of 2-(substituted)-4-hydroxy-5-pyrimidine carboxylic acid, such as the acid chloride, with the appropriate D-N-(trimethylsilyl)-2-substituted glycine, trimethylsilyl ester in the presence of triethylamine followed by hydrolysis.

The silylated amino acid starting materials can be prepared by reacting an anhydrous compound of the formula

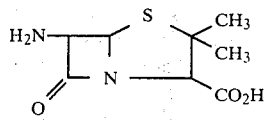

with a hexaalkyldisilazane. The preferred silylating agent is hexamethyldisilazane. Only the carboxyl group is silylated under the conditions used (e.g., 2-hour reflux in dichloromethane). After acrylation, the silyl group is easily removed by treatment with water.

The free acids of the invention form carboxylate salts with any of a variety of inorganic and organic bases. Pharmaceutically acceptable carboxylate salts are formed by reacting the free acids with such bases as sodium hydroxide, sodium carbonate, sodium bicarbonate, sodium 2-ethylhexanoate, potassium hydroxide, potassium carbonate, potassium 2-ethylhexanoate, calcium hydroxide, ethylamine, 2-hydroxyethylamine, and procaine. Preferred carboxylate salt forms are the alkali metal salts. The carboxylate salts are converted to the free acids by acidification.

The free acids and their carboxylate salts usually differ somewhat in solubility properties but, in general, are otherwise equivalent for the purposes of the invention. In addition, certain of the compounds of the invention can exist in the form of an acid-addition salt. Pharmaceutically acceptable salts are formed by reaction of the free base or a basic salt with any of a number of inorganic and organic acids, including hydrochloric, sulfuric, nitric, phosphoric, acetic, benzoic, citric, maleic, malic, tartaric, succinic, gluconic, ascorbic, sulfamic, pamoic, methanesulfonic, benzenesulfonic, and related acids.

When forming salts, certain compounds may form mono, di, or tri, etc., salts. All of these compounds are intended to be equivalent for the purposes of the invention and are intended to fall within the scope of the invention.

The compounds of the invention can exist in anhydrous form, as well as in solvated, including hydrated, forms. In general, the hydrated forms and the solvated forms with pharmaceutically acceptable solvents are equivalent to be anhydrous or unsolvated forms for the purposes of the invention.

The pyrimidine segment of the compounds of this invention may be capable of undergoing keto-enol tautomerism to give 4-keto or 4-hydroxy forms. Such a keto tautomer is equivalent to the shown 4-hydroxy structures for the purposes of the inventions and is included within the above shown structures.

The compounds of the present invention can exist in various sterioisomeric forms. More specfically, the newly introduced amino acid fragments of the compounds may be in the form of the D-isomer, L-isomer or a mixture thereof [DL-mixture partial or complete racemization]. The invention is intended to include all of the isomeric forms and mixtures thereof. Even when a specific form is cited, small amounts of its stereoisomer may be present, since racemization may occur during the various steps in preparing the compound.

The compounds of the invention are new chemical compounds that are useful as pharmacological agents and especially as broad spectrum antibacterial agents. They are active in vitro against strains of both gram-positive and gram-negative bacteria. The activity of the compounds is illustrated by the results shown in the table.

Thus, the compounds of this invention and their nontoxic pharmaceutically acceptable salts are highly useful as broad spectrum antibiotics in mammals when administered in amounts ranging from about 5 mg to 100 mg per kg of body weight per day. A preferred dosage regimen for optimum results would be from about 10 mg to about 50 mg per kg of body weight per day, and such dosage units are employed that a total of about 700 mg to about 3500 mg of active ingredient for a subject of about 70 kg body weight are administered in a 24 hour period in an appropriate pharmaceutical composition.

While the compounds of this invention may be administered orally in the form of tablets, capsules, syrups, etc., the preferred route of administration is parenterally for treating systemic infections.

pyrimidinylcarbonyl]amoxicillin as the sodium salt. $[\alpha]_D^{23} + 148°$ (cl, 75% DMF/pyridine).
$E_1^1$ 348λ317 mμ pH 7

EXAMPLE 2

N-[2-[4-(N-Carbamoylglycylamino)phenyl]-4-hydroxy-5-pyrimidinylcarbonyl]amoxicillin ACTIVITY TABLE
Minimal Inhibitory Concentration

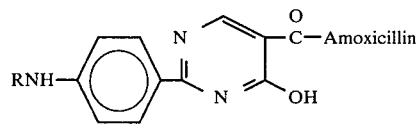

| R | Pseudomonas Aeruginosa UI-18 | Pseudomonas Aeruginosa #28 | Enterobacter Cloacae IMM-11 | Klebsiella Pneumoniae MGH-2 | Serratia Marcescens IMM-16 | Staph Aureus UC-76 | Proteus Vulgaris 1810 |
|---|---|---|---|---|---|---|---|
| N-Acetyl Glycyl | 6.3 | 1.6 | 6.3 | 50 | 6.3 | 0.8 | 1.6 |
| N-Carbamoyl Glycyl | 1.6 | 0.8 | 25 | 50 | 25 | 0.8 | 3.1 |
| N-Acetyl-L-Alanyl | 0.8 | 1.6 | 6.3 | 50 | 12.5 | 0.4 | 0.8 |
| N-Acetyl-DL-Alanyl | 1.6 | 1.6 | 6.3 | 25 | 6.3 | 0.2 | 0.8 |
| N-Propionyl-L-Alanyl | 0.8 | 1.6 | 3.1 | 50 | 12.5 | 0.8 | 3.1 |
| N-Acetylamino Isobutyryl | 0.8 | 0.8 | 6.3 | >50 | 12.5 | 1.6 | 0.4 |
| N-Acetyl-DL-Prolyl | 1.6 | 1.6 | 12.5 | 50 | 12.5 | 0.8 | 1.6 |
| N-Acetyl-beta-Alanyl | 0.8 | 0.8 | 6.3 | 25 | 6.3 | 0.4 | 0.8 |
| N-Acetyl-DL-Methionyl | 1.6 | 1.6 | 12.5 | 50 | 12.5 | 1.6 | 3.1 |
| N-Acetyl-DL-Valyl | 1.6 | 1.6 | 25 | >50 | 25 | 3.1 | 3.1 |
| N-Acetyl-DL-Leucyl | 3.1 | 3.1 | 25 | >50 | 25 | 1.6 | 3.1 |
| N-Acetyl-L-Glutaminyl | 3.1 | 3.1 | 12.5 | >50 | 25 | 3.1 | 0.8 |
| 5-Oxo-L-Prolyl | 1.6 | 0.8 | 6.3 | 50 | 12.5 | 0.8 | 0.8 |
| N-Acetyl-L-Hydroxyprolyl | 1.6 | 1.6 | 12.5 | 50 | 50 | 0.8 | 3.1 |
| N-Acetyl-L-Tyrosyl | 3.1 | 1.6 | 12.5 | 50 | 12.5 | 1.6 | 3.1 |
| N,N'-Diacetyl-DL-Lysyl | 3.1 | 1.6 | 25 | >50 | 50 | 1.6 | 6.3 |
| (2-Oxo-1-pyrrolidinyl) acetyl | 3.1 | 1.6 | 12.5 | 25 | 25 | 1.6 | 1.6 |

In the present invention the term "pharmaceutical composition" is defined as a finished pharmaceutical that may be administered directly or a pharmaceutical which water is added to prior to use in order to form a satisfactory product for administration. The pharmaceutical compositions to be employed parenterally are generally supplied in a dry, sterile form having about 50 mg to about 1000 mg of active compound per vial. The vial may also contain other active ingredients, buffers, salts, etc. The sterile material in the vial is dissolved in water for injection at the time of use. Oral preparations would also have from about 50 mg to about 1000 mg of active compound per unit dose form.

The invention is illustrated by the following examples.

EXAMPLE 1

N-[2-[4-N-Acetylglycylamino)pheny]-4-hydroxy-5-pyrimidinylcarbonyl]amoxicillin

To a cold suspension of 3.3 g (5.5 mmol) of amoxicillin dimethyl sulfoxide complex in 35 ml of diemthylformamide is added 2.0 g (5.25 mmol) of 2-[4-(N-acetylglycylamino)phenyl]-4-hydoxy-5-pyrimidine carboxylic acid imidazolide, followed by 0.77 ml (5.5 mmol) of triethylamine. The solution clears after 30 min at room temperature. After stirring 2 hrs at ambient temperature, the solution is poured into 150 ml of ice water and acidified to pH 2.5 with hydrochloric acid. The precipitate is filtered, washed with water and suspended in ice water. The pH is brought to 6.3 with sodium hydroxide and the filtered solution is lyophilized affording 3.09 g of N-2-[4-(N-acetylglycylamino)-phenyl]-4-hydroxy-5-

To 2.4 g (4.0 mmol) of amoxicillin dimethyl sulfoxide complex in 20 ml of dimethylacetamide is added 1.25 g of 2-[4-(N-carbamoylglycylamino)phenyl]-4-phenyl-5-pyrimidine carboxylic acid imidazolide (3.3 mmol) and the mixture stirred at room temperature for 3 hrs. After filtering through Celite, 1 ml of 3.3 M solution of sodium 2-ethylhexanoate in dimethylacetamide is added. The mixture is added dropwise with stirring to 150 ml of ethyl acetate and the solid is filtered and washed with ether and dried. The solid is dissolved in water (250 ml) and acidified to pH 2.8 with HCl. The precipitate is filtered, washed with water and suspended in 280 ml of water. The pH is raised to 5.6 with sodium hydroxide, filtered and lyophilized to give 2.2 g of N-[2-[4-(N-carbamoylglycylamino)phenyl]-4-hydroxy-5-pyrimidinylcarbonyl]amoxicillin as the sodium salt.
$E_1^1$ 355λ317 mμ pH 7.

EXAMPLE 3

N-[2-[4-(N-Acetyl-L-alanylamino)phenyl]-L-hydroxy-5-pyrimidinylcarbonyl]amoxicillin To a suspension of 3.6 g (6.0 mmol) of amoxicillin dimethyl sulfoxide complex in 15 ml of dimethylformamide is added 0.75 (5.4 mmol) of triethylamine followed by 2.2 g (5.58 mmol) of the imidazolide of 2-[4-(N-acetyl-L-alanylamino)phenyl]-4-hydroxy-5-pyrimidine carboxylic acid. The mixture is stirred for 3 hrs at room temperature and poured into 100 ml of ice water. The pH is lowered to 2.5 with HCl and the precipitate filtered and washed with cold water. The precipitate is suspended in water and pH raised to 5.2 with aqueous alkali. The solution is filtered and lyophilized affording 3.46 g of N-[2-[4-(N-acetyl-L-alanylamino)phenyl]-4- hydroxy-5-pyrimidinylcarbonyl]amoxicillin as the sodium salt. $[\alpha]_D^{23} +83.2°$ (cl, pH 7).

$E_1^1$ 350λ317 mμ pH 7.

EXAMPLE 4

N-[2-[4-(N-Acetyl-DL-alanylamino)phenyl]-4-hydroxy-5-pyrimidinyl-carbonyl]amoxicillin A suspension of 6.2 g (10.2 mmol) of amoxicillin dimethyl sulfoxide complex and 50 ml of N,N-dimethylacetamide is stirred at 5°* and 3.94 g (10 mmol) of 2-[4(N-acetyl-DL-alanylamino)phenyl]-4-hydroxy-5-pyrimidine carboxylic acid imidazolide is added followed by 1.0 ml (7.2 mmol) of triethylamine. The reaction is stirred at 5° for 1 hr and 0.3 (2.2 mmol) of triethylamine is added and stirring is continued at 5° for 2.5 hrs. The reaction mixture is filtered and the filtrate added dropwise to 350 ml of ethyl acetate. The precipitated solid is filtered, washed with ethyl acetate and ether, and air dried. The solid is dissolved in 100 ml of ice water and the pH adjusted to 2.4 with 1 N hydrochloric acid. The acid is filtered washed with ice water and resuspended in cold water. The pH is adjusted to 5.2 with 1 N sodium hydroxide. The solution is clarified by filtration and the filtrate lyophilized to give 5.4 g of N-[2-[4-(N-acetyl-DL-alanylamino)phenyl]-4-hydroxy-5-pyrimidinylcarbonyl]-amoxicillin as the sodium salt. $[\alpha]_D^{25} +112°$ (cl, pH 7).

All temperatures are stated in degrees Centrigrade.

$E_1^1$ 330λ317 mμ pH 7.

EXAMPLE 5

N-[2-[4-(N-Propionyl-L-alanylamino)phenyl]-4-hydroxy-5-pyrimidinylcarbonyl]amoxicillin To a suspension of 2.0 g (3.3 mmol) amoxicillin dimethyl sulfoxide complex in 8 ml dimethylacetamide is added 1.3 g (3.18 mmol) of 2-[4-(N-propionyl-L-alanylamino)phenyl]-4-hydroxy-5-pyrimidine carboxylic acid imidazolide and the mixture stirred for 1.5 hrs at room temperature. To the mixture is added 1 ml of 3.3 M sodium 2-ethyl hexanoate in dimethylacetamide and the solution added to 150 ml of ethyl acetate with stirring. The salt is filtered, washed with ethyl acetate, ether and dried. The product is dissolved in 80 ml water and the pH adjusted to 2.5 with dilute HCl. After filtration and washing with cold water, the solid is suspended in water and the pH adjusted to 5.0 with dilute sodium hydroxide. Lyophilization affords 2.13 g of N-[2-[4-(N-propionyl-L-alanylamino)phenyl]-4-hydroxy-5-pyrimidinylcarbonyl]amoxicillin as the sodium salt. $[\alpha]_D^{24} +61°$ (cl, pH 7).

$E_1^1$ 352λ317 mμ pH 7.

EXAMPLE 6

N-[2-[4-(alpha-Acetamidoisobutyrylamino)phenyl]-4-hydroxy-5-pyrimidinylcarbonyl]amoxicillin To a suspension of 4.2 g (6.6 mmol) of amoxicillin dimethyl sulfoxide complex in 20 ml of dimethylacetamide is added 2.40 g (6 mmol) of the 2-[4-(alpha-acetamidoisobutyrylamino)phenyl]-4-hydroxy-5-pyrimidine carboxylic acid imidazolide followed by 0.8 ml (6.0 mmol) of triethylamine. Immediate solution resulted and the reaction is let stand at room temperature for 3 hrs. Sodium 2-ethylhexanoate (2.1 ml, 6 mmol) is then added, and the resulting solution is precipitated by adding to 300 ml ethyl acetate. The solid is filtered, washed with ether, dried in vacuo and then added to 100 ml of water, acidified to pH 2.5 with 1 N HCl. The solid is filtered, suspended in 200 ml of ice water, stirred and filtered. The solid is again suspended in 100 ml of water, the pH is adjusted to pH 6.5 with 1 N sodium hydroxide and the resulting solution freeze dried to give 2.9 g of N-[2-[4-(alpha-acetamidoisobutyrylamino)phenyl]-4-hydroxy-5-pyrimidinylcarbonyl]-amoxicillin as the sodium salt. $[\alpha]_D^{23} +131°$ (cl, pH 7).

$E_1^1$ 311λ317 mμ pH 7.

EXAMPLE 7

N-[2-[4-(N-Acetyl-DL-prolylamino)phenyl]-4-hydroxy-5-pyrimidinylcarbonyl]amoxicillin A solution of 4.2 g (10 mmol) of 2-[4-(N-acetyl-DL-prolylamino)phenyl]-4-hydroxy-5-pyrimidine carboxylic acid imidazolide, 6.5 g (10 mmol) of amoxicillin dimethylsulfoxide complex, 1.4 ml (10 mmol) triethylamine and 75 ml dimethylacetamide is stirred with ice bath cooling for 2 hrs. The solution is poured into 375 ml of ethyl acetate with stirring. The solid is collected and washed with ethyl acetate and ether to give 7.2 g of crude product. The solid is dissolved with water and acidified to pH 2 with 1 N HCl. The solid is filtered and washed with water. The solid is suspended in water and 1 N sodium hydroxide added until the pH is raised to 6.5. The solution is filtered and freeze dried to give 5.1 g of N-[2-[4-N-acetyl-DL-prolylamino)phenyl]-4-hydroxy-5-pyrimidinylcarbonyl]amoxicillin as the sodium salt. $[\alpha]_D^{23} +146°$ (cl, 75% DMF/pyridine).

$E_1^1$ 326λ318 mμ pH 7.

EXAMPLE 8

N-[2-[4-(N-Acetyl-beta-alanylamino)phenyl]-4-hydroxy-5-pyrimidinylcarbonyl]amoxicillin To a suspension of 6.95 g (11.0 mmol) of amoxicillin dimethylsulfoxide complex in 50 ml of dimethylacetamide is added 3.94 g (10-mmol) of 2-[4-(N-acetyl-beta-alanylamino)phenyl]-4-hydroxy-5-pyrimidine carboxylic acid imidazolide and 1.4 ml (10 mmol) of triethylamine. After stirring at room temperature for 3 hrs the mixture is poured into ice water (200 ml) and acidified to 2.3 with HCl. The product is filtered, washed with water and suspended in 100 ml of water. The pH is raised to 6.0 with sodium hydroxide and the filtered solution lyophilized affording 3.9 g of N-[2-[4-(N-acetyl-beta-alanylamino)phenyl]-4-hydroxy-5-pyrimidinylcarbonyl]amoxicillin as the sodium salt. $[\alpha]_D^{23} +143°$ (cl, pH 7).

$E_1^1$ 328λ217 mμ pH 7.

EXAMPLE 9

N-[2[4-(N-Acetyl-DL-methionylamino)phenyl]-4-hydroxy-5-pyrimidinylcarbonyl]amoxicillin To a suspension of 6.32 g (10 mmol) of amoxicillin dimethyl sulfoxide complex in 75 ml of dimethylacetamide is added 4.55 g (10 mmol) of 2-[4-(N-Acetyl-DL-methionylamino)phenyl]-4-hydroxy-5-pyrimidine carboxylic acid imidazolide followed by 1.4 ml (10 mmol) of triethylamine. The mixture is stirred at room temperature for 3 hrs and poured into 375 ml of ethyl acetate. The solid is collected by filtration and washed with ethyl acetate and ether. The dried solid is dissolved in 100 ml of water and acidified to pH 2.5 with dilute HCl. The solid is filtered and washed with water. The solid is suspended in water, the pH raised to 6.5 with 1 N sodium hydroxide and the filtered solution lyophilized to give 6.4 g of N-[2-[4-(N-acetyl-DL-methionylamino)-phenyl]-4-hydroxy-5-pyrimidinylcarbonyl]amoxicillin as the sodium salt. $[\alpha]_D^{23} +139°$ (cl, 75% DMF/pyridine).

$E_1^1$ 340 λ mμ pH 7.

EXAMPLE 10

N-[2-[4-(N-Acetyl-DL-valylamino)phenyl]-4-hydroxy-5-pyrimidinylcarbonyl]amoxicillin To a stirred suspension of 6.32 g (10 mmol) of amoxicillin dimethyl sulfoxide complex and 1.4 ml (10 mmol) of triethylamine in 75 ml of dimethylformamide is added 4.22 g (10 mmol) of 2-[4-(N-acetyl-DL-valylamino)phenyl]-4-hydroxy-5-pyrimidine carboxylic acid imidazolide. After stirring 10 min at 5° C. and 2 hrs at room temperature the solution is poured into 500 ml of ice water and acidified to 2.5 with 1 N HCl. The solid is filtered, washed well with cold water and resuspended in cold water. The pH is adjusted to 6.6 with 1 N sodium hydroxide and the solution is filtered and lyophilized affording 5.9 g of the N-[2-[4-(N-acetyl-DL-valylamino)phenyl]-4-hydroxy-5-pyrimidinylcarbonyl]amoxicillin as the sodium salt. $[\alpha]_D^{27} +143°$ (cl, 75% DMF/yridine).

$E_1^1$ 326λ317 mμ pH 7.

EXAMPLE 11

N-[2-[4-(N-Acetyl-DL-leucylamino)phenyl]-4-hydroxy-5-pyrimidinylcarbonyl]amoxicillin To a stirred suspension of 2.75 g (4.35 mmol) of amoxicillin dimethyl sulfoxide complex and 0.61 ml (4.35 mmol) of triethylamine in 25 ml of dimethylacetamide at 5° C. is added 1.90 g (4.35 mmol) of the 2-[4-(N-acetyl-DL-leucylamino)phenyl]-4-hydroxy-5-pyrimidine carboxylic acid imidizolide. After stirring for 10 min at 5° C. and 3.75 hrs at room temperature the solution is poured into 250 ml of ice water. The pH is adjusted to 2.5 with 1 N HCl, filtered and washed well with ice water. The solid is suspended in water, the pH adjusted to 6.7 with 1 N sodium hydroxide, filtered and lyophilized affording 2.8 g of N-[2-[4-(N-acetyl-DL-leucylamino)phenyl]-4-hydroxy-5-pyrimidinylcarbonyl]-amoxicillin as the sodium salt. $[\alpha]_D^{25} +139°$ (cl, 75% DMF/pyridine).

$E_1^1$ 298λ316 mμ pH 7.

EXAMPLE 12

N-[2-[4-(N-Acetyl-DL-glutaminylamino)phenyl]-4-hydroxy-5-pyrimidinylcarbonyl]amoxicillin A suspension of 3.30 g (5.23 mmol) of amoxicillin dimethyl sulfoxide complex, 2.34 g (5.23 mmol) of 2-[4-(N-acetyl-DL-glutaminylamino)phenyl]-4-hydroxy-5-pyrimidine carboxylic acid imidazolide and 0.73 ml of triethylamine (5.23 mmol) in 40 ml of dimethylacetamide is stirred for 10 min at 5° and 3 hrs at room temperature. The solution is poured into 250 ml of ice water and the pH is lowered to 2.5 with dilute HCl. The product is filtered and washed well with cold water. The solid is suspended in water, the pH adjusted to 6.7 with 1 N sodium hydroxide and the solution is filtered and lyophilized affording 2.0 g of N-[2-[4-(N-acetyl-DL-glutaminylamino)phenyl]-4-hydroxy-5-pyrimidinylcarbonyl]amoxicillin as the sodium salt. $[\alpha]_D^{23} +123°$ (cl, 75% DMF/pyridine)

$E_1^1$ 328λ317 mμ pH 7.

EXAMPLE 13

N-[2-[4-[(5-oxo-L-prolyl)amino]phenyl]-4-hydroxy-5pyrimidinylcarbonyl]amoxicillin A mixture of 2.55 g (6.5 mmol) of 2-[4-((5-oxo-L-prolyl)amino)phenyl]-4-hydroxy-5-pyrimidine carboxlic acid imidazolide, 4.49 g (6.5 mmol) of amoxicillin, 0.91 ml (6.5 mmol) triethylamine and 50 ml of dimethylacetamide is stirred with ice bath cooling for 1 hour and at room temperature for 3 hrs. The solution is poured into 350 ml of ice and water and acidified to pH 2 with 1 N HCl. The precipitated solid is collected, suspended in water and filtered again. The solid is suspended in water and the pH is adjusted to 6.5 with 1 N sodium hydroxide and the solution is filtered and lyophilized to give 2.2 g of the N-[2-[4-((5-oxo-L-prolyl)amino)-phenyl]-4-hydroxy-5-pyrimidinylcarbonyl]amoxicillin as the sodium salt. $[\alpha]_D^{23} +135°$ (cl, pH 7).

$E_1^1$ 368λ315 mμ pH 7.

EXAMPLE 14

N-[2-[4-(N-Acetyl-L-hydroxyprolylamino)phenyl]-4-hydroxy-5-pyrimidinylcarbonyl]amoxicillin A solution of 3.15 g (4.7 mmol) of amoxicillin dimethyl sulfoxide complex in N,N-dimethylacetamide is stirred at 0°–5° C. and 2.1 g (4.3 mmol) of 2-[4-(N-acetyl-L-hydroxyprolylamino)phenyl]-4-hydroxy-5-pyrimidine carboxylic acid N-hydroxy-succinimide ester cooled in N,N-dimethylacetamide is added. The total volume of N,N-dimethylacetamide is 35 ml. The reaction is stirred in an ice bath for 2½ hrs and for another hour after the bath is removed. The solution is poured into 420 ml cold ethyl acetate. A precipitate is formed which is filtered, resuspended in 400 ml cold ethyl acetate, filtered and air-dried.

To the first ethyl acetate filtrate is added 1.19 ml (4.3 mmol) of sodium 2-ethyl hexanoate and a precipitate is formed. The solid is filtered resuspended in cold ethyl acetate, filtered and dried. This solid combined with the solid from above is taken up in water and the pH adjusted to 2 with dilute hydrochloric acid. The solids are filtered, washed with ice water and resuspended in ice water and filtered. The product is suspended in ice water and the pH adjusted to 6 with dilute sodium hydroxide. The resulting solution is lyophilized to give 1.8 g of N-[2-[4-(N-acetyl-L-hydroxyprolylamino)phenyl]-4-hydroxy-5-pyrimidinylcarbonyl]amoxicillin as the sodium salt. $[\alpha]_D^{23} +108°$ (cl, pH 7).

$E_1^1$ 310λ317 mμ pH 7.

EXAMPLE 15

N-[2-[4-(N-Acetyl-L-tyrosylamino)phenyl]-4-hydroxy-5-pyrimidinylcarbonyl]amoxicillin A suspension of 4.08 g (6.47 mmol) of amoxicillin dimethyl sulfoxide complex, 3.15 g (6.47 mmol) of 2-[4-(N-acetyl-L-tyrosylamino)phenyl]hydroxy-5-pyrimidine carboxylic acid imidazolide, and 0.91 ml (6.47 mmol) of triethylamine in 50 ml of dimethylacetamide is stirred for 10 min at 5° C. and 3 hrs at room temperature. The solution is poured into 300 ml of ice water and the pH is lowered to 2.5 with dilute HCl. The product is filtered, washed well with water and suspended in 150 ml water. The pH is raised to 6.5 with 1 N sodium hydroxide and the filtered solution is lyophilized affording 3.8 g of N-[2-[4-(N-acetyl-L-tyrosylamino)phenyl[-

4-hydroxy-5-pyrimidinylcarbonyl]amoxicillin as the sodium salt. $[\alpha]_D^{23} + 162°$ (cl, pH 7).

$E_1^1$ 301λ317 mμ pH 7.

EXAMPLE 16

N-[2-[4-(N,N'-Diacetyl-DL-lysylamino)phenyl]-4-hydroxy-5-pyrimidinylcarbonyl]amoxicillin A mixture of 4.8 g (7.1 mmol) of amoxicillin dimethyl sulfoxide complex and 3.2 g (6.5 mmol) of 2-[4-(N,N'-diacetyl-DL-lysylamino)phenyl]-4-hydroxy-5-pyrimidine carboxylic acid imidazolide in 45 ml of dimethylacetamide is stirred for 15 min at 5° C. and 2 hrs at room temperature. The solution is poured into 150 ml of ice water and the pH adjusted to 2 with dilute HCl. The product is filtered, washed with ice water and resuspended in water. After adjusting the pH to 6.5 with 1 N sodium hydroxide, the filtered solution is lyophilized affording 4.0 g of N-[2-[4-(N,N'-diacetyl-DL-lysylamino)phenyl]-4-hydroxy-5-pyrimidinylcarbonyl]amoxicillin as the sodium salt.

$[\alpha]_D^{23} + 133°$ (cl, pH 7).

$E_1^1$ 304λ317 mμpH 7.

EXAMPLE 17

N-[2-[4-[(2-Oxo-1-pyrrolidinyl)acetylamino]phenyl]-4-hydroxy-5-pyrimidinylcarbonyl]amoxicillin A mixture of 4.7 g (7.7 mmol) of amoxillin dimethyl sulfoxide complex and 2.85 g (7 mmol) of 2-[4-[(2-oxo-1-pyrrolidinyl)-acetylamino]phenyl]-4-hydroxy-5-pyrimidine carboxylic acid imidazolide is stirred in 25 ml dimethyl sulfoxide for 3 hrs at room temperature and 1.1 ml (7.7 mmol) triethylamine is added. The solution is poured into 300 ml of stirring ethyl acetate and the precipitated triethylamine salt is collected and washed with ethyl acetate. The filtercake is dissolved in 300 ml water at 0°-5° C. and the pH is lowered to 2.5 with 1 N hydrochloric acid. The precipitate is filtered, washed with cold water, and resuspended in 150 ml water at 0°-5° C. and the pH is brought to 7 with 1N sodium hydroxide solution. The solution is filtered and the filtrate is lyophilized leaving 4.0 g of the sodium salt of the title penicillin as a pale yellow solid.

$[\alpha]_D^{23} + 124°$ (cl, pH 7).

$E_1^1$ 322λ317 mμ pH 7.

STARTING MATERIALS

A. 2-(4-Aminophenyl)-4-hydroxy-5-pyrimidine carboxylic acid

A solution of 14.8 g (0.642 mmol) of sodium in 750 ml of dry ethanol is stirred at 0° and 44.6 g (0.214 mmol) of 4-aminobenzamidine .2HCl [Shaw and Cooley, J. Am. Chem. Soc., 79, 3561 (1957)] is added. The mixture is stirred 5 minutes under nitrogen and 46.2 g (0.214 mmol) of diethyl ethoxymethylenemalonate is added. After stirring for 30 min, the mixture is refluxed for 4 hrs and allowed to stand overnight at room temperature. The salt is filtered and washed with isopropanol. The salt is suspended in 214 ml of 2 N potassium hydroxide and stirred at 70° C. for 4 hrs. After treating with a small amount of charcoal, the filtrate is added to 325 ml of 2 N HCl with stirring. The acid is filtered, washed with water, ethanol, and ether, and dried to give 50.8 g of the title compound, mp 312°-314° C. dec. The product is recrystallized from dimethylacetamide-water to give 44.5 g mp 313°-314° C. dec.

| $E_1^1$ | 920 | λ331 | mμ | ⎫ | pH 7 |
|---|---|---|---|---|---|
|  | 460 | 227 |  | ⎭ |  |

B. 2-[4-(N-Benzyloxycarbonylglycylamino)phenyl]-4-hydroxy-5-pyrimidine carboxylic acid A suspension of 9.2 g (40 mmol) of 2-(4-aminophenyl)-4-hydroxy-pyrimidine-5-carboxylic acid in 300 ml of dichloromethane is stirred at room temperature and 12.1g (120 mmol) of triethylamine is added followed by 13.1 g (120 mmol) of trimethylsilyl chloride. The mixture is stirred for 2 hrs at room temperature and then is added to the solution below.

A solution of 8.4 g (40 mmol) of N-benzyloxycarbonylglycine and 200 ml of dichloromethane is stirred at −20° C. and 4.1 g (40 mmol) of triethylamine is added followed by 4.3 g (40 mmol) of ethyl chloroformate. The mixture is stirred at −20° C. for 30 minutes and the above silylated product is then added as rapidly as possible while maintaining the temperature at −20° C. After stirring for 2 hrs at −20° C. and 4 hrs at 5° C., the mixture is allowed to come to room temperature overnight. Methanol (50 ml) is added with stirring and the product separates as a yellow solid. The solid is filtered and washed with dichloromethane and finally ether. The solid is suspended in water, filtered, and washed with ethanol and finally ether. Drying affords 9.5 g of the title compound, mp 254°-260° C. dec. Recrystallization from aqueous dimethylformamide raises the melting point to 276°-277° C. dec.

C. 2-[4-(N-Glycylamino)phenyl]-4-hydroxy-5-pyrimidine carboxylic acid

A solution of 40 ml of 30% HBr in acetic acid is stirred at room temperature and 4.5 g (10.7 mmol) of the above N-benzyloxycarbonylglycyl compound is added. After vigorous carbon dioxide evolution a copious precipitate forms. The mixture is stirred for 2 hrs at room temperature and then cooled in ice. Ethyl acetate (100 ml) is added and the solid is filtered, washed well with ethyl acetate and finally ether. The dried solid is added to 100 ml of cold water and the pH raised to 10.2 with conc. ammonium hydroxide. The solution is filtered and the filtrate concentrated in vacuo. The product crystallizes as needles as the ammonia evaporates. The neutral mixture is filtered and the product washed with water, ethanol and finally ether. The dried title compound weighs 2.57 g, mp 312°-313° C. dec. The product can be readily acylated to form the N-acetyl side chain.

$E_1^1$ 788λ310 mμ}pH 7-50% MeOH.

D. 2-[4-(N-Acetylglycylamino)phenyl]-4-hydroxy-5-pyrimidine carboxylic acid imidazolide A suspension of 2.4 g (8 mmol) of 2-[4-(N-glycylamino)phenyl]-4-hydroxy-5-pyrimidine carboxylic acid and 20 ml of dimethylformamide is stirred at room temperature and 5.5 ml (39 mmol) of triethylamine and 2.0 ml (21 mmol) of acetic anhydride are added. After standing 2 hours at room temperature the solution is poured into 50 ml of ice water and acidifid to pH 2 with HCl. The product is filtered, washed with water, ethanol and finally ether. The dried 2-[4-(N-acetylglycylamino)phenyl]-4-hydroxy-5-pyrimidine carboxylic acid weighs 2.3 g, mp 313°–315° C. dec.

$E_1^1$ 587 λ308 mμ}pH 7.

A suspension of 1.96 g (5.5 mmol) of the above pyrimidine carboxylic acid and 30 ml of dimethylformamide is stirred and 2.0 g (12 mmol) of carbonyldiimidazole is added. The mixture is heated to 55°–60° C. for 30 minutes and stirred at room temperature for 3 hours. Acetonitrile (40 ml) is added and the solid is filtered, washed with acetonitrile and either to give 2.02 g of the title imidazolide.

E.
2-[4-(N-Carbamoylglycylamino)phenyl]-4-hydroxy-5-pyrimidine carboxylic acid imidazolide A solution of 0.928 g (3.2 mmol) of 2-[4-(N-glycylamino)phenyl]-4-hydroxy-5-pyrimidine carboxylic acid and 25 ml of water is treated with 1 ml (7.2 mmol) of triethylamine followed by 1.3 g (16 mmol) of potassium cyanate. After standing at room temperature overnight a 0.5 g (6.2 mmol) portion of potassium cyanate is added and the reaction mixture is allowed to stand at room temperature for another 18 hrs. The solution is concentrated in vacuo to ⅓ its volume and acidified to pH 2.5 with hydrochloric acid. The product is filtered, washed with water, ethanol, and ether to give 1.0 g of 2-[4-(N-carbamoylglycylamino)phenyl]-4-hydroxy-5-pyrimidine carboxylic acid.

$E_1^1$ 608 λ308 mμ}pH 7.

A mixture of 1.31 g (3.75 mmol) of the above pyrimidine carboxylic acid and 20 ml of dimethyl sulfoxide is stirred at room temperature and 1.62 g (10 mmol) of carbonyldiimidazole is added. The mixture heated at 50°–60° C. with stirring for one hour. After standing overnight the product is isolated by adding a mixture of 100 ml acetonitrile and 30 ml ether. The solid is filtered, washed with acetonitrile, ether, and dried to give 1.27 g of the title imidazolide.

F.
2-[4-(N-Acetyl-L-alanylamino)phenyl]-4-hydroxy-5-pyrimidine carboxylic acid imidazolide A suspension of 114.5 g (0.495 mol) of 2-(4-aminophenyl)-4-hydroxy-5-pyrimidine carboxylic acid in 2.97 liters of dichloromethane is stirred at room temperature and 208 ml (1.48 mol) of triethylamine is added followed by 208 ml (1.63 mol) of trimethylsilyl chloride added dropwise over 15 minutes. The mixture is allowed to stir at room temperature for 1.5 hrs and then added to the mixture below.

A suspension of 129.8 g (0.99 mol) of N-acetyl-L-alanine and 2.97 liters of acetonitrile is stirred at room temperature and 109 ml (0.99 mol) of N-methylmorpholine is added. The stirred mixture is cooled to −17° C. and 84.1 ml (0.99 mol) of methyl chloroformate is added dropwise at this temperature and the mixture is stirred at −15° C. for 30 minutes. The mixture is then cooled to −30° C. and the silylated mixture from above is added over a period of 5 minutes keeping the temperature at −15° C. The mixture is stirred for 4 hrs at 0° C. and allowed to stand overnight at room temperature. The reaction mixture is concentrated to a solid in vacuo and 4 liters of water is added to the residue. The pH of the suspension is adjusted to 7.5 with alkali and the solution is clarified by filtration. After three extractions with 300 ml portions of methylene chloride, the aqeous layer is acidificed to pH2 with 12% hydrochloric acid. The solid is removed by filtration and washed with water.

The wet cake is then washed with 750 ml isopropanol-ether (1:1) and then with ether and dried to give 147 g of 2-[4-(N-acetyl-L-alanylamino)phenyl]-4-hydroxy-5-pyrimidine carboxylic acid; mp 226° C. dec.

$[\alpha]_D^{23}$ −72.5° (cl, pH 8).

$E_1^1$ 632 λ309 mμ}pH 7.

A suspension of 2.38 grams (6.92 mmol) of the above acylated pyrimidine carboxyklic acid and 10 ml of dimethylformamide is stirred at room temperature and 2.0 g (12.3 mmol) of carbonyldiimidazole is added. The stirred mixture is heated at 50°–60° C. for 1 hr and allowed to stand at room temperature for 3 hrs. The solvent is removed in vacuo and the residue is crystallized by the addition of dichloromethane. The product is filtered, washed with dichloromethane and ether, and dried to give 1.95 g of the title imidazolide; mp 222° C. dec.

G.
-[4-(N-Acetyl-DL-alanylamino)phenyl)]-4-hydroxy-5-pyrimidine carboxylic acid imidazolide The silylated derivative of 2-(4-aminophenyl)-4-hydroxy-5-pyrimidine carboxylic acid is prepared as described in Starting Material F from 11.55 g (50 mmol) of the acid, 20.8 ml (148 mmol) of triethylamine, and 20.8 ml (163 mmol) of trimethylsilyl chloride in 300 ml of dichloromethane.

A solution of 13.1 g (100 mmol) of DL-acetyl-alanine and 300 ml of acetonitrile is stirred at room temperature and 10.1 g (100 mmol) of N-methylmorpholine is added. After cooling to −15° C., 10.4 g (110 mmol) of methyl chloroformate is added and the reaction mixture is stirred for 30 min at −15° C. The above silylated solution is added and the mixture stirred overnight at room temperature. The mixture is evaporated to dryness in vacuo, 150 ml of water is added, and the pH is adjusted to 2.0 with hydrochloric acid. The solid is filtered, washed with water, isopropanol and ether and dried to give 15.5 g of 2-[4-(N-acetyl-DL-alanylamino)phenyl]-4-hydroxy-5-pyrimidine carboxylic acid; mp 271°–272° C.

$E_1^1$ 635 λ309 mμ pH 7.

A suspension of 3.0 g (8.75 mmol) of the above acid and 30 ml of dimethylformamide is stirred at room temperature and 3.0 g (18.5 mmol) of carbonyldiimidazole is added. The reaction mixture is heated at 50°–60° C. for 0.5 hr and stirred at room temperature overnight. Dichloromethane (25 ml) and ether (50 ml) are added and the solid filtered, washed with ether, and dried to afford 3.2 g of the title imidazolide.

H.
2-[4-(N-Propionyl-L-alanylamino)phenyl]-4-hydroxy-5-pyrimidine carboxylic acid imidazolide A solution of 5.67 g (30 mmol) of N-t-butoxycarbonyl-L-alanine in 75 ml of acetonitrile is stirred at 0° and 6.36 g (63 mmol) of N-methylmorpholine is added and the mixture cooled to −20° C. Next 3.62 g (30 mmol) of pivaloyl chloride is added and the mixture stirred at −15° C. for 1.5 hrs and a solution cooled to −10° C., containing 3.46 g (15 mmol) of 2-(4-aminophenyl) 4-hydroxy-5-pyrimidine carboxylic acid, 75 ml of acetonitrile, and 4.17 ml (30 mmol) of triethylamine is added. After stirring for 2 hrs at −10° C. the mixture is then kept at room temperature for 18 hrs. The solution is evaporated to near dryness in vacuo and treated with 200 ml of water. The pH is adjusted to 2.8 with citric acid and the product filtered, washed with water and ether, and dried to give 5.8 g of 2-[4-(N-t-butoxycarbonyl-L-alanylamino)phenyl]-4-hydroxy-5-pyrimidine carboxylic acid. $[\alpha]_D^{23}$ −28.5° (cl, pH 7).

$E_1^1$ 484 λ309 mμ}pH 7.

A solution of 20 ml trifluoroacetic acid and 2 ml of anisole is stirred at 5° C. and 2.8 g (6.97 mmol) of the above protected pyrimidine carboxylic acid is added. After stirring for 1.5 hrs at 5° C. the solution is evaporated in vacuo and treated with 150 ml ether with stirring. The solid is filtered, washed with ether, and dried. The solid is suspended in cold water and the pH adjusted to 4.5 with sodium hydroxide and the 2-[4-(N-L-alanylamino)phenyl]-4-hydroxy-5-pyrimidine carboxylic acid which is filtered, washed with water and dried in vacuo, weighs 1.90 g.

A suspension of 1.90 g (6.3 mmol) of the above pyrimidine acid and 20 ml of pyridine is stirred at room temperature and 5 ml of propionic anhydride is added. After stirring 1 hr at room temperature, methanol (10 ml) is added and the mixture evaporated to a syrup in vacuo. Water is added to the residue, the pH is adjusted to 2.3 with dilute HCl, and the product filtered. After washing with water and drying gives 1.93 g of 2-[4-(N-propionyl-L-alanylamino)phenyl]-4-hydroxy-5-pyrimidine carboxylic acid; mp 247°–248° C. $[\alpha]_D^{25}$ −81° (cl, pH 7).

$E_1^1$ 586 λ309 mμ}pH 7.

A suspension of 1.38 g (3.8 mmol) of the above propionyl derivative and 8 ml of dimethylformamide is stirred at room temperature and 1.3 g (8 mmol) of carbonyldiimidazole is added. The mixture is stirred at 50°–60° C. for 1 hr and at room temperature for 3 hrs. The product is precipitated with 40 ml of ether and the ether is decanted and the product washed again with ether. The residue is suspended in warm acetonitrile and cooled and the solid filtered washed with acetonitrile and ether to give 1.20 g of the title imidazolide.

I.

2-[4-(alpha-Acetamidoisobutyrylamino)phenyl]-4-hydroxy-5-pyrimidine carboxylic acid imidazolide A suspension of 41.2 g (0.4 mmol) of alpha-aminoisobutyric acid, 100 ml pyridine, and 100 ml water is stirred at 0°–5° C. and 45.0 ml (0.45 mmol) of acetic anhydride is added over a period of 30 min. Solution is observed after 1 hr and the mixture is allowed to stand at room temperature for 10 hrs. The reaction mixture is diluted with 500 ml water and evaporated in vacuo. The residue is then recrystallized from water, dried in vacuo affording 37.0 g alpha-acetamidoisobutyric acid.

A mixture of 11.6 g (80 mmol) of alpha-acetamidoisobutyric acid, 8.8 ml (80 mmol) of N-methylmorpholine, and 200 ml acetonitrile is cooled to −20° C., 6.0 ml (80 mmol) of methyl chloroformate is added. The mixture is stirred at −10° C. to −5° C. for 20 minutes and a solution of the silylated 2-(4-aminophenyl)-4-hydroxy-5-pyrimidine carboxylic acid (prepared as described in Starting Material F from 9.2 g (40 mmol) of the acid, 16.8 ml (120 mmol) of triethylamine, and 15.4 ml (120 mmol) of trimethylsilyl chloride in 400 ml of dichloromethane) is added dropwise. After the addition, the mixture is stirred in an ice bath for 3 hrs, then at room temperature for 12 hrs. Two ml of isopropanol are added to the mixture and it is stirred for 20 min and the solid filtered. The filtrate is evaporated in vacuo and the residue triturated in water, filtered, and dried to yield 5.6 g of 2-[4-(alpha-acetamidoisobutyrylamino)phenyl]-4-hydroxy-5-pyrimidine carboxylic acid.

A mixture of 5.6 g (15.7 mmol) of the above pyrimidine acid and 5.0 g (31 mmol) of carbonyldiimidazole in 100 ml tetrahydrofuran is stirred at 50° C. for ½ hr and at room temperature for 2 hrs. The mixture is filtered and the solids washed with ether and dried in vacuo affording 4.75 g of the title imidazolide.

J.

2-[4-(N-Acetyl-DL-prolylamino)phenyl]-4-hydroxy-5-pyrimidine carboxylic acid imidazolide A solution of 13.2 g (84 mmol) of N-acetyl-DL-proline in 150 ml of dichloromethane is stirred at −10° C. and 11.8 ml (84 mmol) triethylamine is added followed by 11.0 ml (84 mmol) of isobutyl chloroformate. The reaction mixture is stirred at −10° C.±5° C. for ½ hr and a cold solution of 12.94 g (56 mmol) of 2-(4-aminophenyl)-4-hydroxy-5-pyrimidine carboxylic acid and 8.6 ml (61.6 mmol) triethylamine in 200 ml N, N-dimethylacetamide is added. The reaction solution is stirred at 0°–5° C. for 3 hours and overnight at room temperature. The reaction mixture is evaporated and the residue triturated with water. The mixture is filtered to give 3.5 g of solid. On standing, more solid crystallizes out of the aqueous filtrate. Filtration gives an additional 11.5 g of 2-[4-(N-acetly-DL-prolylamino)phenyl]-4-hydroxy-5-pyrimidine carboxylic acid; mp 269°–271° C. dec.

$E_1^1$ 590 λ309 mμ}pH 7.

A mixture of 7.4 g (20 mmol) of (2-[4-(N-acetyl-DL-prolylamino)phenyl]-4-hydroxy-5-pyrimidine carboxylic acid and 6.48 g (40 mmol) of carbonyldiimidazole in 75 ml of tetrahydrofuran is stirred at 51°–52° C. for 1 hr and at room temperature overnight. The reaction mixture is filtered and the solid washed with tetrahydrofuran and ether giving 5.8 grams of the title imidazolide.

K.

2-[4-(N-Acetyl-beta-alanylamino)phenyl]-4-hydroxy-5-pyrimidine carboxylic acid imidazolide A solution of 4.6 g (35 mmol) of N-acetyl-beta-alanine, 100 ml acetonitrile, and 3.9 ml (35 mmol) of N-methylmorpholine is stirred at −15° C. and 5.0 ml (38.5 mmol) of isobutyl chloroformate is added. After 30 minutes at −15° C. a solution prepared from 4.05 g (17.5 mmol) of 2-(4-aminophenyl)-4-hydroxy-5-pyrimidine carboxylic acid, 7.35 ml (52.5 mmol) of triethylamine, and 7.96 ml (62.7 mmol) of trimethylsilyl chloride in 100 ml of dichloromethane is added and the mixture stirred at −10° C. for 1 hour and at room temperature overnight. The mixture is evaporated to near dryness in vacuo and treated with 200 ml of water. The product is precipitated by acidifying to pH 2.0 and is filtered, washed with water, isopropanol, ether, and dried to give 5.8 g of 2-[4-(N-acetyl-beta-alanylamino)phenyl]-4-hydroxy-5-pyrimidine carboxylic acid.

$E_1^1$ 640λ310 mμ}pH 7.

A suspension of 5.7 g (16.5 mmol) of the above pyrimidine acid, 20 ml of dimethylformamide, and 5.7 g (35.1 mmol) of carbonyldiimidazole is stirred at 50°–60° C. for 30 minutes and 3 hrs at room temperature. Acetonitrile (40 ml) and ether (40 ml) are added and the product filtered, washed with acetonitrile, ether, and dried to give 6.3 g of the title imidazolide.

L.
2-[4-(N-Acetyl-DL-methionylamino)phenyl]-4-hydroxy-5-pyrimidine carboxylic acid imidazolide A suspension of 14.34 g (75 mmol) of N-acetyl-DL-methionine and 150 ml of dichloromethane is stirred at −15° C. and 10.5 ml (75 mmol) of triethylamine is added followed by 9.75 ml (75 mmol) of isobutyl chloroformate. After stirring for 20 minutes at −15° C., a solution of 11.6 g (50 mmol) of 2-(4-aminophenyl)-4-hydroxy-5-pyrimidine carboxylic acid in 200 ml of dimethylacetamide containing 7.7 ml (55 mmol) of triethylamine is added at −15° C. The mixture is stirred at 0° C. for 3 hrs and overnight at room temperature. The mixture is evaporated and the residue triturated with water. The aqueous suspension, after adjusting the pH to 2.5 with dilute HCl is filtered, washed with water, and dried to give 11.54 g of 2-[4-(N-acetyl-DL-methionylamino)phenyl]-4-hydroxy-5-pyrimidine carboxylic acid; mp 259° C. dec.

$E_1^1$ 508λ309 mμ} pH 7.

A mixture of 2.04 g (4.9 mmol) of the above pyrimidine carboxylic acid, 1.6 g (9.8 mmol) of carbonyldiimidazole, and 25 ml of dimethylformamide is stirred at 50°–60° C. for 30 min and allowed to stand at room temperature overnight. The solvent is removed in vacuo and the residue treated with 50 ml of tetrahydrofuran and 200 ml of ether. The solid is filtered, washed with tetrahydrofuran, ether, and dried to give 2.04 g of the title imidazolide.

M.
2-[4-(N-Acetyl-DL-valylamino)phenyl]-4-hydroxy-5-pyrimidine carboxylic acid imidazolide A suspension of 11.94 g (75 mmol) of N-acetyl-DL-valine, 10.5 ml (75 mmol) of triethylamine, and 150 ml of dichloromethane is stirred at −15° C. and 9.75 ml (75 mmol) of isobutyl chloroformate is added. The mixture is stirred at −15° C. for 30 min and a cold solution of 11.6 g (50 mmol) of 2-(4-aminophenyl)-4-hydroxy-5-pyrimidine carboxylic acid and 7.7 ml (55 mmol) of triethylamine in 200 ml of N,N-dimethylacetamnide is added at −15° C. After stirring for 3 hrs at 0° C. the mixture is allowed to stand overnight at room temperature. The solvent is removed in vacuo and water is added to the residue. The pH is lowered to 2.0 with 1N hydrochloric acid and the solid is filtered, washed with water, isopropanol, ether, and dried to afford 8.0 g of 2-[4-(n-acetyl-DL-valylamino)phenyl]-4-hydroxy-5-pyrimidine carboxylic acid; mp 275°–278° C. dec.

$E_1^1$ 585λ309 mμ} pH 7.

A mixture of 4.05 g (10.7 mmol) of the above pyrimidine carboxylic acid, 3.4 g (22 mmol) of carbonyldiimidazole, and 50 ml of dimethylformamide is stirred at 50°–60° C. for 30 min and stirred at room temperature for 3 hrs. The solvent is removed in vacuo and the residue treated with 50 ml of tetrahydrofuran and 100 ml ether. The product is filtered, washed with tetrahydrofuran and ether, and dried affording 3.43 g of the title imidazolide.

N.
2-[4-(N-Acetyl-DL-leucylamino)phenyl]-4-hydroxy-5-pyrimidine carboxylic acid imidazolide A solution of 13.0 g (75 mmol) of N-acetyl-DL-leucine, 10.5 ml (75 mmol) of triethylamine, and 150 ml of dichloromethane is stirred at −10° C. and 9.75 ml (75 mmol) of isobutyl chloroformate is added. The reaction mixture is stirred for ½ hour at −10° C. and a cold solution of 11.6 g (50 mmol) of 2-(4-aminophenyl)-4-hydroxy-5-pyrimidine carboxylic acid and 7.7 ml (55 mmol) of triethylamine in 200 ml of dimethylformamide is added. The mixture is stirred at 5° C. for 3 hrs and overnight at room temperature. The reaction mixture is evaporated and the residue treated with water. The pH is lowered to 2.5 with dilute hydrochloric acid and the solid filtered, washed with water, and dried to give 13.8 g of 2-[4-(N-acetyl-DL-leucylamino)-phenyl]-4-hydroxy-5-pyrimidine carboxylic acid; mp 233°–235° C. dec.

$E_1^1$ 434λ308 mμ}pH 7.

A mixture of 3.86 g (10 mmol) of the above pyrimidine carboxylic acid and 3.24 g (20 mmol) of carbonyldiimidazole in 50 ml of dimethylformamide is stirred at 50°–60° C. for 30 min and allowed to stand at room temperature overnight. The solvent is removed in vacuo and the residue treated with 50 ml of ether. Filtration, washing with tetrahydrofuran and ether, and drying affords 1.90 g of the title imidazolide.

O.
2-[4-(N-Acetyl-DL-glutaminylamino)phenyl]-4-hydroxy-5-pyrimidine carboxylic acid imidazolide A solution of 14.1 g (75mmol) of N-acetyl-L-glutamine and 9.75 ml (75 mmol) of triethylamine in 150 ml of dimethylformamide is stirred at −15° to −20° C. and 9.75 ml (75 mmol) of isobutyl chloroformate is added. After stirring at −15° to −20° C. for 30 min a cold solution of 11.6 g (50 mmol) of 2-(4-aminophenyl)-4-hydroxy-5-pyrimidine carboxylic acid and 7.15 ml (50 mmol) of N-methylmorpholine in 200 ml of dimethylformamide is added at −15° C. The reaction mixture is stirred at −15° C. for 20 min at 5° C. for 3 hrs, and at room temperature overnight. The reaction mixture is evaporated and the residue treated with water. The pH is lowered to 2.5 with hydrochloric acid and the solid is filtered, washed with water, and dried to afford 17.3 g of 2-[4-(N-acetyl-DL-glutaminylamino)phenyl]-4-hydroxy-5-pyrimidine carboxylic acid; mp 247°–248° C. dec. $[\alpha]_D^{25}$ −2.8 (c0.7, DMSO).

$E_1^1$ 487λ310 mμ}pH 7.

A mixture of 4.01 g (10 mmol) of the above pyrimidine carboxylic acid and 3.24 g (20 mmol) of carbonyldiimidazole in 50 ml of dimethylformamide is stirred at 50°–60° C. for 30 min and allowed to stand overnight at room temperture. The solvent is removed in vacuo and the residue treated with 50 ml of tetrahydrofuran and 200 ml of ether. The solid is filtered, washed with tetrahydrofuran and ether, and dried affording 2.38 g of the title imidazolide.

P.
2-[4-[(5-Oxo-L-prolyl)amino]phenyl]-4-hydroxy-5-pyrimidine carboxylic acid imidazolide A suspension of 12.9 g (0.1 mol) 5-oxo-L-proline, 7.7 ml (0.1 mol) dimethylformamide, and 150 ml of dichloromethane is stirred at 0°–5° C. and 7.3 ml (0.1 mol) of thionyl chloride is added. The reaction mixture is stirred at 0°–5° C. for ½ hrs and at room temperature for 2 hrs. After stirring for 20 minutes at room temperature a solution of 11.55 g (0.05 mmol) of 2-(4-aminophenyl)-4-hydroxy-5-pyrimidine carboxylic acid, 7.7 ml (0.55 mmol) triethylamine, and 150 ml of dimethylformamide is added and stirred at 0°–5° C. for 1 hr and at room temperature overnight. The reaction mixture is filtered and the solid is washed with dichloromethane, methanol, water, methanol, and ether to give 13.3 g of 2-[4-[(5-oxo-L-prolyl)amino]phenyl]-4-hydroxy-5-pyrimidine carboxylic acid; mp>300° C.

$E_1^1$ 639λ308 mμ}pH 7.

A mixture of 13.3 g (38.85 mmol) of the above pyrimidine acid, 12.59 g (77.7 mmol) of carbonyldiimidazole and 100 ml of dimethylformamide is stirred at 54°–59° C. for ½ hr and at room temperature for 16 hrs. Acetonitrile (100 ml) and ether (100 ml) are added to the reaction solution. The precipitated solid is filtered, washed with ether, and dried to yield 7.7 g of the title imidazolide.

Q.
2-[4-(N-Acetyl-L-hydroxyprolylamino)phenyl]-4-hydroxy-5-pyrimidine carboxylic acid N-hydroxysuccinimide ester The silylated derivative of 2-(4-aminophenyl)-4-hydroxy-5-pyrimidine carboxylic acid is prepared from 10 g (43.2 mmol) of the acid, 18.06 ml (130 mmol) of triethylamine, and 17.1 ml (130 mmol) of trimethylsilyl chloride in 800 ml of dichloromethane as described in Starting Material F.

A suspension of 22.4 g (129 mmol) of N-acetyl-L-4-hydroxyproline and 300 ml of dichloromethane is stirred at −10° C. and 18.06 ml (130 mmol) of triethylamine is added, followed by 10.2 ml (130 mmol) of methyl chloroformate at −10° C. to −15° C. The silylated acid solution from above is added in aliquots keeping the temperature below −5° C. When all is added, the reaction temperature is allowed to rise to 0° C. and the reaction flask is placed in an ice bath. The reaction is stirred overnight allowing the bath temperature to rise to room temperature. The reaction is filtered and filtrate is evaporated. Water is added to the residue and the mixture is stirred for 2 hrs and filtered. The product is resuspended in water, stirred, and filtered. The solid is taken up in isopropanol and a light precipitate is filtered off. The filtrate is evaporated down and the residue is washed with isopropanol and ether. The product is suspended in water and cooled in an ice bath. The pH is adjusted to 2.15 with dilute hydrochloric acid and the precipitate is filtered. The solid is taken up in isopropanol and the insolubles filtered off. The solids are dissolved in methanol and added to the isopropanol solution. The resulting solution is evaporated down and ether added to the residue. A light yellow solid is obtained and dried under vacuum to give 8.8 g of 2-[4-(N-acetyl-L-hydroxypropylamino)phenyl]-4-hdyroxy-5-pyrimidine carboxylic acid.

A solution of 3.0 g of (7.8 mmol) of the above pyrimidine acid and 1.0 g (8.6 mmol) of hydroxysuccinimide in N,N-dimethylacetamide is stirred in an ice bath and 2.0 g (9.5 mmol) of dicyclohexylcarbodiimide in N,N-dimethylacetamide is added giving a total volume of 30 ml of N,N-dimethylacetamide. The reaction is stirred overnight. Ether is added to the reaction mixture and the resulting oil is triturated into a solid by the addition of isopropanol. The solid is filtered, washed with isopropanol and dried to give 2.11 g of the title activated ester.

R.
2-[4-N-Acetyl-L-tyrosylamino)phenyl]-4-hydroxy-5-pyrimidine carboxylic acid imidazolide A suspension of 10.08 g (45 mmol) of N-acetyl-L-tyrosine and 4.95 ml (45 mmol) of N-methylmorpholine in 100 ml of dichloromethane is stirred at −15° C. and 5.88 ml (45 mmol) of isobutyl chloroformate is added. After stirring for 30 min at −15° C. a cold solution of 6.93 g (30 mmol) of 2-(4-aminophenyl)-4-hydroxy-5-pyrimidine carboxylic acid and 3.63 ml (33 mmol) of N-methylmorpholine in 120 ml of dimethylacetamide is added. The mixture is stirred at 5° C. for 3 hrs and at room temperature overnight. The solvents are removed in vacuo, water is added to the residue and the pH is adjusted to 2.0 with dilute HCl. The product is filtered, washed with water, and dried to give 3.59 g of 2-[4-(N-acetyl-L-tyrosylamino)phenyl-4-hydroxy-5-pyrimidine carboxylic acid.

A mixture of 3.58 g (8.2 mmol) of the above pyrimidine carboxylic acid and 2.66 g (16.4 mmol) carbonyldiimidazole in 50 ml of dimethylformamide is stirred at 50°–60° C. for 30 min. After standing at room temperature for 2-½ hrs, solvent is removed in vacuo and 50 ml of tetrahydrofuran is added followed by 200 ml of ether. The solid is filtered, washed with tetrahydrofuran and ether to afford 3.17 g of the title imidazolide.

S.
2-[4-(N,N′-Diacetyl-DL-lysylamino)phenyl]-4-hydroxy-5-pyrimidine carboxylic acid imidazolide The silylated derivative of 2-(4-aminophenyl)-4-hydroxy-5-pyrimidine carboxylic acid is prepared from 4.64 g (20 mmol) of the acid, 6.3 g (63 mmol) of triethylamine, and 6.8 g (63 mmol) of trimethylsilyl chloride in 160 ml of dichloromethane as described in Starting Material F.

A solution of 9.2 g (40 mmol) of N,N′-diacetyl-DL-lysine and 4.06 g (42 mmol) of N-methylmorpholine in 100 ml of 1:1 dimethylacetamide-dichloromethane is stirred at −12° C. and 5.7 g (42 mmol) of isobutyl chloroformate is added. The mixture is stirred at −12° C. for 25 min and the cold (5°) silylsated acid solution from above is added over 30 min at −12° C. After stirring at 5° C. for 2 hrs and at room temperature overnight, 15 ml of isopropanol is added and the solid is filtered washed with isopropanol and water and dried to give 7.1 g of 2-[4-(N,N′-diacetyl-DL-lysylamino)phenyl]-4-hydroxy-5-pyrimidine carboxylic acid; mp 252°–253° dec.

A stirred suspension of 7.0 g (15.8 mmol) of the above pyrimidine carboxylic acid and 5.2 g (32 mmol) of carbonyldiimidazole in 125 ml of dimethylformamide is stirred at 50°–55° C. for 1 hr and at room temperature for 4 hrs. The product is precipitated by adding 500 ml of acetonitrile. After filtration and washing with acetonitrile and drying 5.8 g of the title imidazolide is obtained; mp 192°–193° C. dec.

$E_1^1$ 443λ323 mμ} pH 7.

T.
2-[4-[(2-Oxo-1-pyrrolidinyl)acetylamino]phenyl]-4-hydroxy-5-pyrimidine carboxylic acid imidazolide A suspension of 8.1 g (35 mmol) 2-(4-aminophenyl)-4-hydroxy-5-pyrimidine carboxylic acid and 75 ml of N,N-dimethylacetamide is stirred at room temperature and 12 ml (85 mmol) of triethylamine is added. The mixture is stirred for 3 hrs until a solution forms.

In a separate flask 7.2 g (50 mmol) of 2-oxo-1-pyrrolidineacetic acid is added to 150 ml of dichloromethane and 50 ml of a 1 M solution of 2-chloro-1-methylpyridinium methylsulfate in dichloromethane.* The mixture is stirred at room temperature and 7 ml (50 mmol) of triethylamine is added in portions, a solution results after ca. 2 hrs of stirring. The two solutions are combined and kept at room temperature for 48 . The dichloromethane is evaporated and the residue is slurried with 700 ml water and brought into solution by adjusting to pH 8 with triethylamine. The pH is then lowered to 3.0 and the precipitated solid is collected, washed with water and acetone and dried to give 12.3 g of 2-[4-[(2-oxo-1-pyrrolidinyl)acetylamino]phenyl]-4-hydroxy-5-pyrimidine carboxylic acid as a pale yellow solid; mp>320° C.

*A stock solution of the coupling reagent can be made conveniently by mixing 38 ml (0.4 mol) 2-chloropyridine and 38 ml (0.4 mol )dimethylsulfate in 340 ml dichloromethane and allowing the bottled solution to react at room temperature for 2 days.

$E_1$ $^{1600\lambda309}$ m$\mu$pH7

A suspension of 6.2 g (17 mmol) of the above pyrimidine acid, 4.9 g (30 mmol) of carbonyldiimidazole and 60 ml of N,N-dimethylacetamide is stirred overnight at room temperature. The mixture is diluted with 100 ml of dichloromethane and the solid is filetered, washed with dichloromethane, and dried to give 7.0 g of the title imidazolide; mp 245°–250° C.

We claim:

1. A compound of the formula

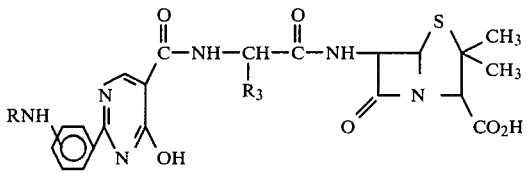

and pharmaceutically acceptable salts thereof; wherein R is

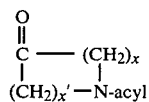

or $R_1[_{NR_4}$-acyl$]_n$; x is an integer from one to five, x' is zero, one or two; $R_1$ is hydrogen, lower alkyl, benzyl or

wherein $R_2$ is hydrogen, amino or a lower alkyl group of from one to four carbon atoms, optionally substituted by from one to three chlorine or fluorine atoms; $R_4$ is hydrogen or lower alkyl; NH-acyl is an aminoacyl moiety derived from a carboxylic acid of from two to ten carbon atoms optionally substituted by from one to three of the following groups, hydroxyl, carboxyl,

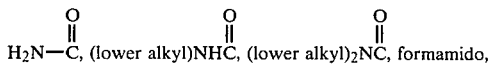

lower alkylamido

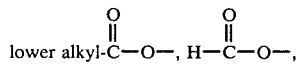

lower alkoxy, lower alkylthio carbamido, amino, carbonyl oxygen or sulfonic acid; $R_3$ is phenyl, 4-hydroxyphenyl, 2-thienyl or cyclohexa-1,4-dien-1-yl and n is an integer of from one to four; when n is two to four, the acyl groups may be the same or different; when the acyl group is substituted by more than one group, the substituents may be the same or different.

2. The compound of claim 1 wherein R-NH is in the para position.

3. The compound of claim 2 wherein NH-acyl is N-acetyl glycyl, N-acetyl-L-alanyl, N-propionyl-L-alanyl, N-acetyl-L-glutaminyl, alpha-acetamidoisobutyryl and 5-oxo-L-prolyl.

4. The compound of claim 3 wherein $R_2$ is a carbon fragment of from one to two carbon atoms.

5. The compound of claim 4 wherein $R_3$ is phenyl or 4-hydroxyphenyl.

6. The compounds of claim 1 having the name N-[2-[4-(N-acetylglycylamino)phenyl]-4-hydroxy-5-pyrimidinylcarbonyl]-amoxicillin or a pharmaceutically acceptable salt thereof.

7. The compound of claim 1 having the name N-[2-[4-(N-carbamoylglycylamino)phenyl]-4-hydroxy-5-pyrimidinylcarbonyl]-amoxicillin or a pharmaceutically acceptable salt thereof.

8. The compound of claim 1 having the name N-[2-[4-(N-acetyl-L-alanylamino)phenyl]-4-hydroxy-5-pyrimidinylcarbonyl]-amoxicillin or a pharmaceutically acceptable salt thereof.

9. The compound of claim 1 having the name N-[2-[4-N-acetyl-DL-alanylamino)phenyl]-4-hydroxy-5-pyrimidinylcarbonyl]-amoxicillin or a pharaceutically acceptable salt thereof.

10. The compound of claim 1 having the name N-[2-[4-(N-propionyl-L-alanylamino)phenyl]-4-hydroxy-5-pyrimidinylcarbonyl]-amoxicillin or a pharmaceutically acceptable salt thereof.

11. The compound of claim 1 having the name N-[2-[4-(alpha-acetamidoisobutyrylamino)phenyl]-4-hydroxy-5-pyrimidinylcarbonyl]amoxicillin or a pharmaceutically acceptable salt thereof.

12. The compound of claim 1 having the name N-[2-[4-(N-acetyl-DL-prolylamino)phenyl]-4-hydroxy-5-pyrimidinylcarbonyl]-amoxicillin or a pharmaceutically acceptable salt thereof.

13. The compound of claim 1 having the name N-[2-[4-(N-acetyl-beta-alanylamino)phenyl]-4-hydroxy-5-pyrimidinylcarbonyl]-amoxicillin or a pharmaceutically acceptable salt thereof.

14. The compound of claim 1 having the name N-[2-[4-(N-acetyl-DL-methionylamino)phenyl]-4-hydroxy-5-pyrimidinylcarbonyl]-amoxicillin or a pharmaceutically acceptable salt thereof.

15. The compound of claim 1 having the name N-[2-[4-(N-acetyl-DL-valylamino)phenyl]-4-hydroxy-5pyrimidinylcarbonyl]-amoxicillin or a pharmaceutically acceptable salt thereof.

16. The compound of claim 1 having the name N-[2-[4-(N-acetyl-DL-leucylamino)phenyl]-4-hydroxy-5-pyrimidinylcarbonyl]-amoxicillin or a pharmaceutically acceptable salt thereof.

17. The compound of claim 1 having the name N-[2-[4-(N-acetyl-DL-glutaminylamino)phenyl]-4-hydroxy-5-pyrimidinyl-carbonyl]-amoxicillin or a pharmaceutically acceptable salt thereof.

18. The compound of claim 1 having the name N-[2-[4-[(5-oxo-L-prolyl)amino]phenyl]-4-hydroxy-5-pyrimidinylcarbonyl]-amoxicillin or a pharmaceutically acceptable salt thereof.

19. The compound of claim 1 having the name N-[2-[4-(N-acetyl-L-hydroxyprolylamino)phenyl]-4-hydroxy-5-pyrimidinylcarbonyl]amoxicillin or a pharmaceutically acceptable salt thereof.

20. The compound of claim 1 having the name N-[2-[4-(N-acetyl-L-tyrosylamino)phenyl]-4-hydroxy-5-pyrimidinylcarbonyl]-amoxicillin or a pharmaceutically acceptable salt thereof.

21. The compound of claim 1 having the name N-[2-[4-(N,N'-diacetyl-DL-lysylamino)phenyl]-4-hydroxy-5-pyrimidinylcarbonyl]-amoxicillin or a pharmaceutically acceptable salt thereof.

22. The compound of claim 1 having the name N-[2-[4-[(2-oxo-1-pyrrolidinyl)acetylamino]phenyl]-4-hydroxy-5-pyrimidinylcarbonyl]amoxicillin and pharmaceutically acceptable salts thereof.

23. An antibacterial pharmaceutical composition; comprising from 50 mg to 1000 mg of a compound of claim 1 and a pharmaceutical carrier.

24. A method for treating antibacterial infections which comprises administering 5 mg to 100 mg per kg of body weight per day of the composition of claim 23, to a mammal having a bacterial infection.

* * * * *